United States Patent
Richter

(10) Patent No.: US 9,289,377 B2
(45) Date of Patent: Mar. 22, 2016

(54) APPARATUS AND METHOD FOR TREATING BODY TISSUES WITH ELECTRICITY OR MEDICAMENTS

(75) Inventor: Jacob Richter, Arsuf (IL)

(73) Assignee: Microtech Medical Technologies Ltd., Tel Aviv (IL)

( * ) Notice: Subject to any disclaimer, the term of this patent is extended or adjusted under 35 U.S.C. 154(b) by 0 days.

(21) Appl. No.: 13/358,758

(22) Filed: Jan. 26, 2012

(65) Prior Publication Data

US 2012/0123320 A1    May 17, 2012

Related U.S. Application Data

(60) Division of application No. 11/313,712, filed on Feb. 9, 2006, now Pat. No. 8,108,041, which is a division of application No. 10/782,762, filed on Feb. 23, 2004, now Pat. No. 7,001,372, which is a division of application No. 09/964,836, filed on Sep. 26, 2001, now abandoned, which is a continuation of application No. 09/360,893, filed on Jul. 26, 1999, now Pat. No. 6,334,859.

(51) Int. Cl.
| | | |
|---|---|---|
| *A61N 1/32* | (2006.01) | |
| *A61K 9/00* | (2006.01) | |
| *A61H 39/00* | (2006.01) | |

(52) U.S. Cl.
CPC ............ *A61K 9/0009* (2013.01); *A61H 39/002* (2013.01); *A61N 1/32* (2013.01)

(58) Field of Classification Search
CPC ...... A61H 39/002; A61N 1/32; A61K 9/0009
USPC ............................ 607/62, 115, 116; 600/439
See application file for complete search history.

(56) References Cited

U.S. PATENT DOCUMENTS

| | | | |
|---|---|---|---|
| 4,041,954 A | 8/1977 | Ohara | |
| 4,351,337 A | 9/1982 | Sidman | |
| 4,585,652 A | 4/1986 | Miller et al. | |
| 4,611,596 A | 9/1986 | Wasserman | |
| 4,651,740 A | 3/1987 | Schroeppel | |
| 4,657,543 A | 4/1987 | Langer et al. | |
| 4,944,659 A | 7/1990 | Labbe et al. | |
| 5,041,107 A | 8/1991 | Heil, Jr. | |
| 5,102,402 A * | 4/1992 | Dror et al. | 604/265 |

(Continued)

FOREIGN PATENT DOCUMENTS

| | | |
|---|---|---|
| CA | 2311730 | 1/2001 |
| EP | 0 061 783 | 10/1982 |

(Continued)

OTHER PUBLICATIONS

Partial European Search Report dated Apr. 21, 2009, 9-pages from co-pending application No. EP 08008616.8, published as EP 2 027 887.

(Continued)

*Primary Examiner* — Tammie K Heller
(74) *Attorney, Agent, or Firm* — Cadwalader Wickersham & Taft LLP

(57) ABSTRACT

A therapeutic device and therapeutic method for delivering electrical energy or medicament to a body tissue or organ utilizing ultrasonic vibration to cause a device implanted in the body tissue or organ to be treated to discharge an electrical current or medicament to the target area.

4 Claims, 3 Drawing Sheets

(56) References Cited

U.S. PATENT DOCUMENTS

| | | | |
|---|---|---|---|
| 5,298,017 | A | 3/1994 | Theeuwes |
| 5,304,206 | A | 4/1994 | Baker et al. |
| 5,366,454 | A | 11/1994 | Currie et al. |
| 5,411,535 | A | 5/1995 | Fujii et al. |
| 5,421,816 | A | 6/1995 | Lipkovker |
| 5,431,694 | A | 7/1995 | Snaper et al. |
| 5,453,653 | A | 9/1995 | Zumeris |
| 5,551,953 | A | 9/1996 | Lattin et al. |
| 5,647,844 | A | 7/1997 | Haak |
| 5,656,016 | A | 8/1997 | Ogden |
| 5,735,280 | A * | 4/1998 | Sherman et al. .......... 600/1 |
| 5,741,317 | A | 4/1998 | Ostrow |
| 5,749,909 | A | 5/1998 | Schroeppel et al. |
| 5,797,898 | A | 8/1998 | Santini, Jr. |
| 5,807,306 | A | 9/1998 | Shapland et al. |
| 5,893,840 | A | 4/1999 | Hull et al. |
| 6,768,919 | B2 | 7/2004 | Starobin et al. |
| 6,969,382 | B2 | 11/2005 | Richter |

FOREIGN PATENT DOCUMENTS

| | | |
|---|---|---|
| EP | 0 495 531 | 7/1992 |
| EP | 1 072 283 A2 | 1/2001 |
| EP | 1 072 283 A3 | 7/2003 |
| EP | 1 072 283 B1 | 8/2008 |
| EP | 2 027 887 A2 | 2/2009 |
| EP | 2 027 887 A3 | 5/2009 |
| JP | 61-196967 | 9/1986 |
| JP | 02-058426 | 8/1988 |
| JP | 63-209649 | 8/1988 |
| JP | 1-502045 | 7/1989 |
| JP | 02-19147 | 1/1990 |
| JP | 2-144077 | 6/1990 |
| JP | 2-152469 | 6/1990 |
| JP | H2-152468 | 6/1990 |
| JP | 4-135571 | 5/1992 |
| JP | 5-220222 | 8/1993 |
| JP | 5-245215 | 9/1993 |
| JP | 5-329482 | 12/1993 |
| JP | 10-503960 | 4/1998 |
| RU | 94/027257 | 5/1996 |
| RU | 2082467 | 6/1997 |
| WO | WO 93/09841 | 5/1993 |
| WO | WO 94/21314 | 9/1994 |
| WO | WO 96/13302 | 5/1996 |
| WO | WO 88/05314 | 7/1998 |
| WO | WO 99/39768 | 8/1999 |
| WO | WO 00/12062 | 3/2000 |
| WO | WO 01/07110 A2 | 2/2001 |
| WO | WO 01/07110 A3 | 5/2001 |
| WO | WO 2004/065541 A2 | 8/2004 |
| WO | WO 2004/065541 A3 | 2/2005 |

OTHER PUBLICATIONS

Office Actions from Parent U.S. Pat. No. 6,334,859, issued Jan. 1, 2002: Non-Final Office Action dated Mar. 6, 2000; Response to Non-Final Office Action w/ Extension of Time dated Sep. 11, 2000; Final Office Action dated Dec. 6, 2000; Amendment and Response After Final Rejection with Extension of Time dated Jun. 15, 2001; Notice of Appeal dated Jun. 15, 2001; Notice of Allowance dated Jun. 25, 2001; Amendment after Notice of Allowance dated Oct. 1, 2001; and Response to Amendment after Notice of Allowance dated Nov. 28, 2001.

Office Actions from Continuation U.S. Appl. No. 09/964,836, filed Sep. 26, 2001, which thereafter was abandoned: Preliminary Amendment dated Sep. 26, 2001; Non-Final Office Action dated Jul. 5, 2002; Response to Office Action with Extension of Time dated Jan. 17, 2003; Requirement of Restriction/Election dated Apr. 9, 2003; Response to Requirement for Restriction/Election with Extension of Time dated Aug. 21, 2003; Final Rejection dated Nov. 21, 2003; and Application abandoned for failure to respond to the outstanding final rejection dated Jun. 2, 2004.

Office Actions from Divisional U.S. Pat. No. 7,001,372 issued Feb. 21, 2006: Required for Restriction/Election dated Jan. 21, 2005; Response to Requirement for Restriction/Election dated Feb. 18, 2005; Non-Final rejection dated May 6, 2005; Response to Non-Final Rejection dated Jun. 20, 2005; and Notice of Allowance dated Sep. 12, 2005.

Office Actions and Response from co-pending Divisional U.S. Appl. No. 11/313,712 field Feb. 9, 2006: Non-Final Rejection dated Mar. 27, 2008; Response to Non-Final Rejection with Extension of Time Dated Jul. 28, 2008; Final Rejection dated Nov. 20, 2008; Response to Final Rejection with Request for Continued Examination dated Feb. 19, 2009; Non-Final Rejection dated Mar. 31, 2009; Response to Non-Final Rejection dated Jun. 30, 2009; Final Rejection dated Oct. 28, 2009; Response to Final Rejection with Request for Continued Examination dated Jan. 28, 2010; Non-Final Rejection dated Mar. 16, 2010; Response to Non-Final Rejection dated Jun. 16, 2010; Notice of Non-Compliant or Non-Responsive Amendment dated Jun. 23, 2010; Response to Non-Final Rejection / Non-Compliant/ Non-Responsive Amendment dated Jul. 8, 2010; Final Rejection dated Sep. 30, 2010; Response to Final Rejection with Request for Continued Examination and Extension of Time dated Jan. 31, 2011; Examiner Interview Summary dated Sep. 20, 2011; and Notice of Allowance dated Sep. 20, 2011.

Office Actions and Responses from Continuation-In-Part U.S. Pat. No. 6,969,382 issued Nov. 29, 2005: Requirement for Restriction/Election dated Oct. 4, 2004; Response to Requirement for Restriction/Election dated Nov. 4, 2004; Non-Final Rejection dated Jan. 28, 2005; Response to Non-Final Rejection with Extension of Time dated May 31, 2005; and Notice of Allowance dated Aug. 10, 2005.

Office Actions and Responses from Continuation U.S. Pat. No. 7,785,319 issued Aug. 31, 2010; Preliminary Amendment dated May 31, 2005; Requirement for Restriction/Election dated Sep. 18, 2007; Response to Requirement for Restriction/Election dated Nov. 15, 2007; Non-Final Rejection dated Apr. 1, 2008; Amendment and Response to Non-Final Rejection with Terminal Disclaimer and Extension of Time dated Aug. 1, 2008; Terminal Disclaimer Decision dated Nov. 24, 2008; Final Rejection dated Nov. 26, 2008; Amendment and Response to Final Rejection with Request for Continued Examination dated Feb. 26, 2009; Examiner Interview Summary Record dated Jun. 5, 2009; Amendment and Response to Non-Final Rejection dated Jul. 28, 2009; Final Rejection dated Dec. 1, 2009; Amendment and Response after Final Rejection with Extension of Time dated Mar. 19, 2010; Applicant Summary of Interview with Examiner dated Apr. 9, 2010; Examiner Summary Record dated Apr. 14, 2010; Notice of Allowance dated Apr. 21, 2010; and Supplemental Notice of Allowance dated Jun. 29, 2010.

* cited by examiner

APPARATUS AND METHOD FOR TREATING BODY TISSUES WITH ELECTRICITY OR MEDICAMENTS

CROSS REFERENCES TO RELATED APPLICATIONS

This application is a division of application Ser. No. 11/313,712, filed 9 Feb. 2006, now U.S. Pat. No. 8,108,041, which is a division of application Ser. No. 10/782,762 filed 23 Feb. 2004, now U.S. Pat. No. 7,001,372, which is a division of application Ser. No. 09/964,836 filed 26 Sep. 2001, abandoned, which is a continuation of application Ser. No. 09/360,893 filed 26 Jul. 1999, now U.S. Pat. No. 6,334,859, each of which is incorporated herein by reference in its entirety.

FIELD OF THE INVENTION

The present invention relates generally to devices which are implanted within the body of a living animal or human to impart a therapeutic benefit to a target tissue. More particularly this invention relates to a device and method for selectively electrically stimulating body tissues or organs and also for selectively delivering a medicament to a target tissue or organ. It is also the intention of this invention to provide improved treatment by reducing the time between the sensing of a specific activity within the tissue or organ being treated and the onset of the delivery of the electrical stimulus or medicament drug to the site of the sensed activity.

BACKGROUND OF THE INVENTION

Many disorders, e.g., brain disorders and certain types of paralysis, are treated by an electrical stimulus or local drug delivered to specific sites in the brain or the body. One shortcoming of conventional treatment devices and procedures is that conventional treatment devices are large and their placement may cause damage to the patient Another shortcoming of conventional treatment devices and procedures is that the devices are often implanted and must remain connected to the outside world for their control signal or energy supply. Another shortcoming of conventional devices and procedures is that drug delivery to the target tissue may cause trauma to the patient and may not be precisely delivered to the target tissue. Another shortcoming of conventional procedures is that the physical connection to the outside world and the repeated trauma to the patient required by repeated invasion and introduction of foreign objects into the tissue increases the likelihood of infection. Yet another shortcoming of conventional devices and procedures is that they do not provide precise timing of the delivery of the electrical stimulus or drug in response to phenomena happening in, and to stimuli generated by, the tissue or the organ being treated indicating the need for the delivery of such an electrical stimulus or drug.

OBJECTS AND SUMMARY OF THE INVENTION

It is an object of this invention to provide an apparatus and method of selectively applying an electrical stimulus over a period of time to a target tissue of the body, e.g., the brain, without creating a large lesion in the target area and without requiring a connection to the outside world, i.e., outside the patient's body. A selective stimulus means a stimulus is specific in time and geometry and may be triggered by tissue activity at the specific location.

It is another object of this invention to provide an apparatus and method for selectively delivering a medicament over a period of time to a target tissue of the body, e.g., the brain, without creating a large lesion in the target area and without requiring a connection to the outside world, i.e., outside the patient's body.

It is yet another object of this invention to provide a method of treating body tissue, comprising the steps of preparing a device capable of generating electrical current at a therapeutic voltage and amperage in response to ultrasonic vibrations; disposing the device in the vicinity of the tissue to be treated; and subjecting the device to ultrasonic vibrations in an amount and for a period of time sufficient for the device to generate electrical currents at a therapeutic voltage and amperage.

It is a further object of this invention to provide a device for treating body tissue, comprising a housing provided with a medicament storage compartment. An oscillating member is attached to the housing and communicates with the medicament storage compartment and is adapted to oscillate in response to ultrasonic stimulation. A medicament port is disposed on the housing and is in fluid communication with the medicament storage compartment and is adapted to permit a medicament to be introduced into and contained in the compartment. The medicament port is further adapted to selectively release the medicament from the medicament storage compartment in response to the oscillations of the oscillating member which produce a 'pumping" action to pump the medicament out of the compartment in response to external high frequency stimulation.

It is still a further object of this invention to provide a method of treating body tissue, comprising the steps of preparing a device comprising a housing provided with a medicament storage compartment. An oscillating member is attached to the housing and is in fluid communication with the medicament storage compartment and is adapted to oscillate in response to ultrasonic stimulation. A medicament port is disposed on the housing and communicates with the medicament storage compartment and is adapted to permit a medicament to be introduced into and contained in the compartment. The medicament port is further adapted to selectively release the medicament from the medicament storage compartment in response to oscillations of the oscillating member. In operation, a medicament is introduced through the medicament port and into the medicament storage compartment. The device is disposed in the vicinity of the tissue to be treated and is subjected to ultrasonic vibrations in an amount and for a period of time sufficient for the oscillating member to oscillate in an amount and for a period of time to cause the desired quantity medicament to be discharged from the medicament storage compartment through the medicament port to the tissue to be treated.

It is yet another object of this invention to provide a sensor or an array of sensors communicating with a tissue or organ being treated, e.g., the brain. The sensors communicate with one or more actuators adapted to selectively deliver a predetermined amount of an electrical impulse or a medicament to the tissue or organ being treated in response to the sensed stimulus generated by the tissue or organ being treated indicating the need for the delivery of such an electrical impulse or medicament. In an especially preferred embodiment, the stimulation is sensed in one tissue, e.g., the brain or a nerve and the stimulation occurs in a different tissue, e.g. 1 a paralyzed leg muscle.

DETAILED DESCRIPTION OF THE INVENTION

Miniature Oscillating Ceramic Motors (OCM) are well known in the art and are disclosed in U.S. Pat. No. 5,453,653 to Zumeris the specification of which is incorporated herein by reference. These motors can be made very small and in any shape and they operate by contacting a surface in an amount sufficient to generate sufficient friction to permit the motor to "crawl" along the contacted surface and change its position relative to the contacted surface when the motor is energized. These motors can be adequately insulated to act in aqueous environments. Their small size and low energy level requirements make them especially suitable for use inside living organisms.

Figure 1:
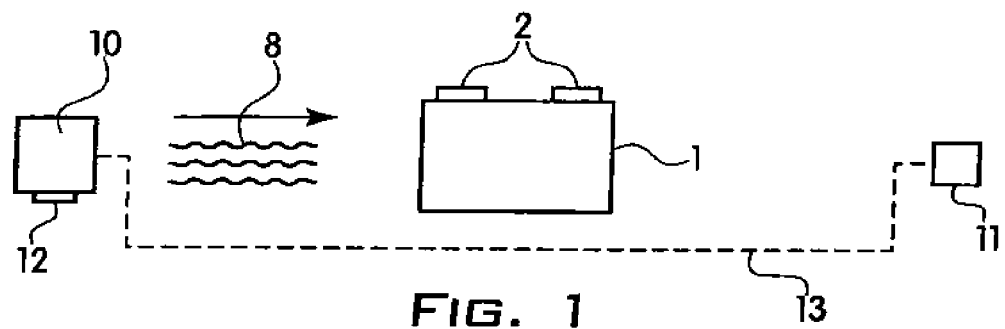
FIG. 1 shows a device constructed in accordance with the invention for applying electrical stimulation to a target tissue.

FIG. 1 shows one embodiment of a ceramic motor used in accordance with the invention to provide electrical stimulation to a target tissue. The electrical stimulation device 1 is provided with electrodes 2. In normal use, electricity is applied to the electrodes 2 which causes the electrical stimulation device 1 to generate oscillations in the ultrasonic range. It is well known that if a conventional electric motor is turned it will produce electricity. Similarly, if the ceramic motor is ultrasonically vibrated an electrical current will be generated and discharged from the electrodes 2. The ceramic motor works according to the second piazo-electric effect, and the reverse, generation of current by vibrating the ceramic is equivalent to the first piazo-electric effect. The frequencies utilized in the various embodiments of this invention may be varied as specific applications dictate. A wide range of frequencies, e.g., radio frequency (rf) or ultrasound (us), may be utilized depending upon the type and the location of the tissue being treated and the type and amount of tissue through which the high frequency vibrations must pass.

The stimulation of nerve cells in the brain system and elsewhere in the body is desirable for the treatment of different disorders, e.g., the activation of muscles whose biological activation is impaired. In application, the device will be delivered to the target area to be treated, e.g., the brain, using conventional procedures such as catheter delivery or surgical implant. Because the electrical stimulation device I is small there is minimal trauma to the patient. In addition, because the electrical stimulation device 1 is left in place there is a reduced likelihood of complications or tissue damage that might result from repeated invasion, e.g., by needles or electrodes repeatedly introduced and removed from the target area. Furthermore, because there is no need for the electrical stimulation device 1 to remain connected to the outside world after it has been implanted, there is a reduced likelihood of complications, e.g., infection, that may result from the connection to the outside world.

Once the electrical stimulation device 1 is in place it is subjected to ultrasonic energy 8 from a means 10 for selectively generating ultrasonic vibrations 8 which causes the electrical stimulation device 1 to vibrate and generate electricity from the electrodes 2. The electrodes 2 may be sized and disposed on the device as specific applications dictate to maximize the effectiveness of the treatment. The electrical stimulation device 1 and the treatment time may be modified to generate electricity at a desired voltage and amperage and for a desired period of time as specific applications dictate.

Figure 2:
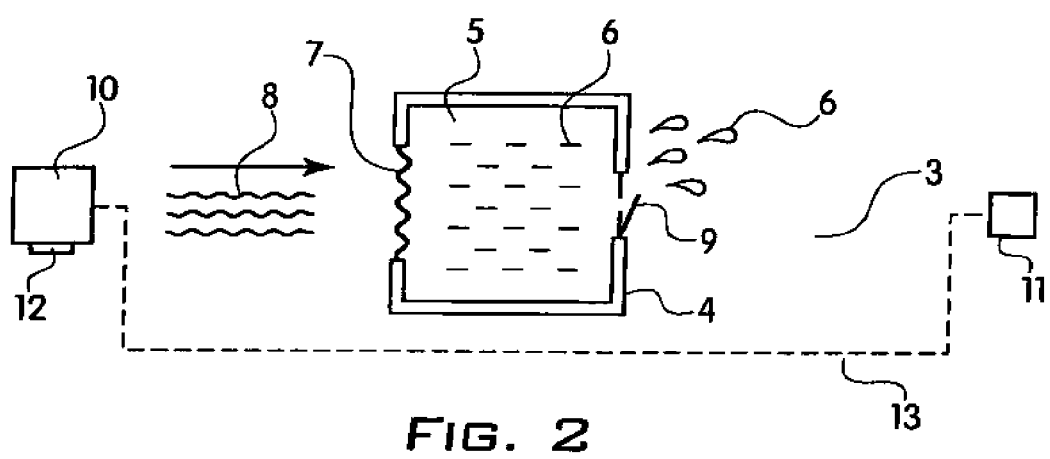
FIG. 2 shows a device constructed in accordance with the invention for delivering a medicament to a target tissue.
Figure 3:
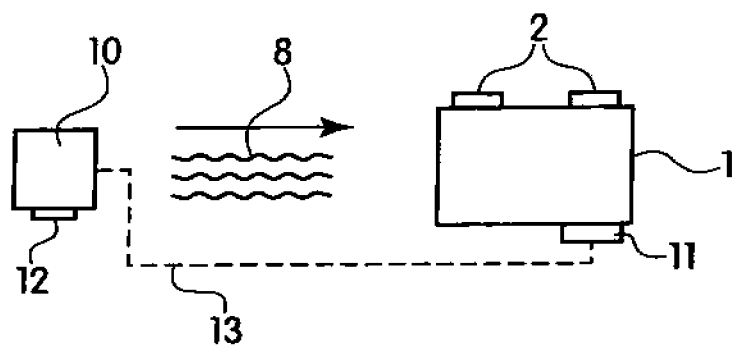
FIG. 3 shows an alternative embodiment of the device shown in FIG. 1.
Figure 4:
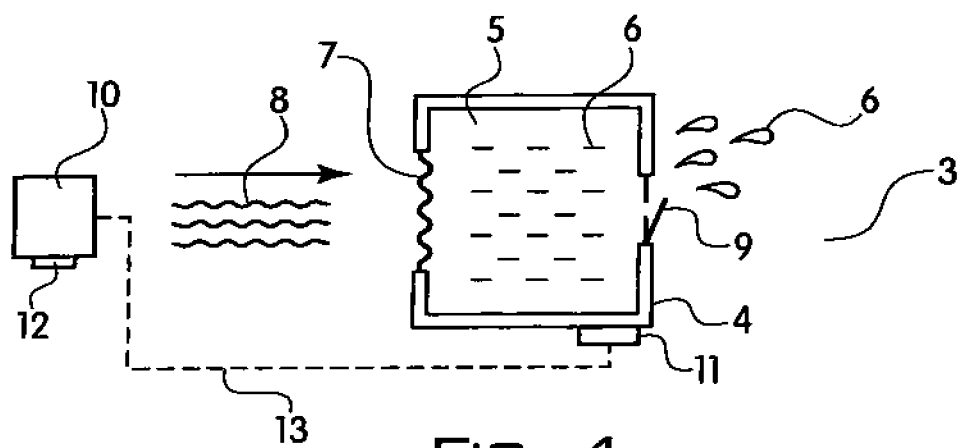
FIG. 4 shows an alternative embodiment of the device shown in FIG. 2.

FIG. 2 shows a medicament delivery device 3 constructed in accordance with the invention. FIG. 2 shows that medicament delivery device 3 is provided with housing 4 provided with a medicament storage compartment 5 for storing a medicament 6. The housing 4 is also provided with an oscillating member 7 constructed of a material that is adapted to oscillate in response to ultrasonic stimulation 8. The oscillating member 7 communicates with the medicament storage compartment 5 so that the oscillating member 7 will contact a medicament 6 stored in the medicament storage compartment 5. The housing 4 is also provided with a medicament port 9 in fluid communication with the medicament storage compartment 5. The medicament port 9 is adapted to permit a medicament 6 to be introduced into the medicament storage compartment 5 and is further adapted to permit the medicament 6 to be discharged from the medicament storage compartment 5 when the oscillating member 7 oscillates. A wide variety of ports or valves well known to those skilled in the art as suitable for this purpose may be utilized, however, in a preferred embodiment an elastic flap valve shown in FIG. 2 is utilized.

In operation, the physician will introduce the medicament 6 into the medicament storage compartment 5 through the medicament port 9. The medicament delivery device 3 is then introduced into the target area using conventional procedures as previously discussed. As shown in FIG. 2, the physician may subject the medicament delivery device 3 to ultrasonic energy 8 generated by a means 10 for selectively generating and transmitting ultrasonic vibrations 8 to the oscillating member 7. The ultrasonic energy 8 impinging upon the oscillating member 7 causes the oscillating member 7 to oscillate as shown in FIG. 2. This causes the desired amount of medicament 6 to be discharged from the medicament storage compartment 5 through the medicament port 9 to the target area. The amount of time that the device 3 is exposed to the ultrasonic vibration 8 can be varied as specific applications dictate and will depend upon factors such as the target area to be treated, the quantity of medicament 6 to be delivered, and the composition, e.g., solid or liquid and/or the viscosity of the medicament 6.

In utilizing both the electrical stimulation device 1 and the medicament delivery device 3, the means for generating the ultrasonic vibrations 10 may be manually operated, may be programmed to generate ultrasonic vibrations for a predetermined fixed period of time, e.g., 10 seconds, at predetermined fixed intervals, e.g., every hour, or may be automatically energized in response to signals received from a sensor 11.

In an especially preferred embodiment one or more sensors 11 are utilized in conjunction with the devices 1 and 3 as shown in FIGS. 1 to 6 to monitor the tissue being treated for a variety of preselected physiological activities and parameters which indicate the need for treatment and the amount of treatment required. These physiological activities and parameters include, e.g., but are not limited to, changes in neurological activity, temperature, pressure, fluid discharge from the target area, chemical composition of the discharge, and chemical changes in the tissue being treated.

The sensor or sensors 11 may be implanted at several points on or in the tissue or organ being treated as specific applications dictate. Alternatively, the sensor 11 may be disposed on the devices 1 and 3 as shown in FIGS. 3-6. The sensor 11 is adapted to communicate with a means 10 for selectively generating and transmitting ultrasonic vibrations 8 as previously discussed. The communication 13 between the sensor 11 and the means 10 for generating ultrasonic vibrations 8 may be a direct one, e.g., by an electrical lead, however, in a preferred embodiment the communication 13 takes place via radio transmission. Radio communication between the sensor 11 and the means for generating ultrasonic vibrations 10 reduces discomfort to the patient and also reduces the likelihood of infection because a wire connection is not required.

Figure 5:
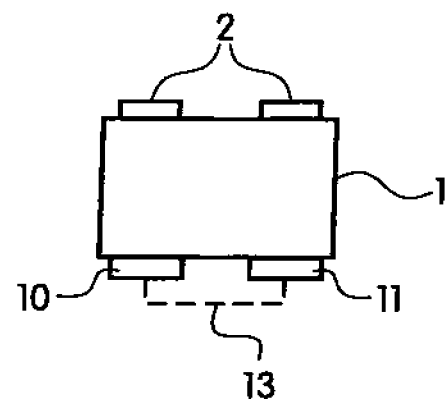
FIG. 5 shows an alternative embodiment of the device shown in FIG. 1.
Figure 6:
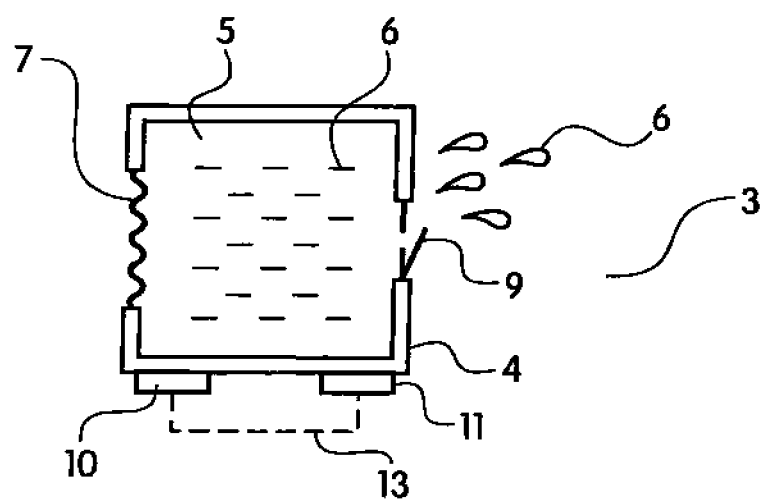
FIG. 6 shows an alternative embodiment of the device shown in FIG. 2.

In operation, the sensor 11 monitors physiological parameters of the tissue or organ being treated and senses changes in these physiological parameters. Upon sensing a change, the sensor 11 sends a signal to the means 10 for generating ultrasonic vibrations 8. In response to the signal received from the sensor 11, the means 10 for generating ultrasonic vibrations 8 generates an ultrasonic signal 8 for a period of time sufficient for the device to deliver the desired treatment to the tissue or organ being treated as previously discussed. The period of time that the ultrasonic signal 8 is generated may be fixed or may be selectively varied depending on the physiological change sensed by the sensor 11 and may be varied as a function of the type and degree of physiological change sensed by the sensor 11. In an especially preferred embodiment, the means 10 for generating the ultrasonic vibration 8 may be provided with a means 12 for calculating the amount of electricity or medicament required by the tissue or organ being treated depending on the type and degree of sensed physiological change. Varying the duration of the ultrasonic vibration 8 generated varies and controls the amount of electricity or medicament delivered to the tissue or organ being treated. Thus, this embodiment provides a self-monitoring and self-delivering system that rapidly calculates the amount of treatment required and provides rapid delivery of the required amount of treatment to the target area. The means 10 for generating the ultrasonic vibration 8 may also be disposed on the devices 1 and 3 as shown in FIGS. 5 and 6 to provide a one piece monitoring, dosage calculating, and administering system.

Alternatively, sensing may occur in one tissue, e.g., the brain or a nerve and the stimulation may occur in a different tissue, e.g., a paralyzed muscle.

The devices and methods of this invention may be modified and adapted for a wide range of treatments as specific circumstances dictate, and more specifically in an especially preferred embodiment, in cases of paralysis. For example, if a person's leg were paralyzed, a stimulator could be provided which would communicate with the muscles of the leg. The stimulator would generate a stimulus to the muscles in response to a sensor that could be located on, or communicate with, e.g., the person's arm. The sensor could be adapted to be responsive to movements of the individual's arm. Thus, when the individual wanted to activate the muscles of his leg he could do so by voluntarily moving his arm a predetermined distance or in a predetermined direction. The sensor in the arm would sense the movement of the arm and generate a signal that would communicate with the stimulator communicating with the muscles in the person's leg. This permits the person to selectively generate a stimulus to the muscles and allow the person to selectively activate the muscles of his leg.

Figure 7:
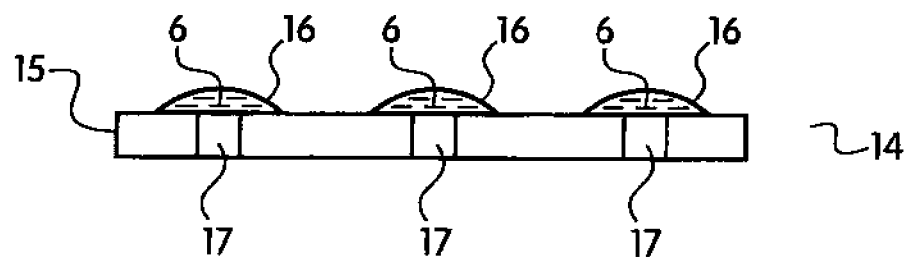
FIG. 7 shows an alternative embodiment of a device constructed in accordance with the invention for delivering a medicament to a target tissue.

FIG. 7 shows medicament delivery device 3 constructed in accordance with the invention for delivering a medicament to a target tissue. FIG. 7 shows that medicament delivery device 14 is provided with housing 15 provided with one or more medicament storage compartment bubbles 16 for storing a medicament 6. The bubbles 16 are constructed of a material well known to those skilled in the art that is selected and adapted to rupture in response to ultrasonic stimulation 8. The housing 15 may also be provided with one or more medicament ports 17 in fluid communication with the medicament storage compartment bubbles 16. The medicament ports 17 are adapted to permit a medicament 6 to be introduced into the medicament storage compartment bubbles 16. A wide variety of ports or valves well known to those skilled in the art as suitable for this purpose may be utilized as previously discussed.

In operation, the physician will introduce the medicament 6 into the medicament storage compartment bubbles 16 through the medicament port 17. The medicament delivery device 14 is then introduced into the target area using conventional procedures as previously discussed. The physician may selectively subject the medicament delivery device 14 to ultrasonic energy as previously discussed. The ultrasonic energy impinging upon the bubbles 16 causes the bubbles 16 to rupture. This causes the desired amount of medicament 6 to be discharged from the medicament storage compartment bubbles 16 to the target area. The amount of time that the device 14 is exposed to the ultrasonic vibration can be varied as specific applications dictate and will depend upon factors such as the target area to be treated, the quantity of medicament 6 to be delivered, the composition, e.g., solid or liquid and/or the viscosity of the medicament 6, and the type of material used to make the storage compartment bubbles 16. In an alternative embodiment, the medicament port is not utilized. Instead, the medicament 6 is disposed between the housing 15 and the bubbles 16 before the bubbles 16 are attached to the housing 15.

The devices and procedures of this invention provide minimally invasive electrical and medicament stimulation of tissue with reduced risk of complications, e.g., infection, that may result from conventional procedures. While the invention has been described with respect to a limited number of embodiments, it will be appreciated that many variations, modifications, and other applications of the invention may be made.

What is claimed is:

1. An implantable device for treating body tissue, comprising:
   a housing provided with a medicament storage compartment bubble, wherein the bubble ruptures in response to ultrasonic stimulation applied to the medicament storage compartment bubble after implantation of the device; wherein said device when implanted operates without physical connection to the outside of a patient's body; and
   a medicament port disposed on the housing and in fluid communication with the medicament storage bubble wherein said medicament port is separately positioned from said medicament storage bubble on the housing, said medicament port adapted to permit a medicament to be introduced into and contained in the medicament storage bubble.

2. The device of claim 1, wherein said medicament port is structured to permit introduction of fluid within said medicament storage bubble.

3. An apparatus for treating body tissue, consisting essentially of:
   a means for generating ultrasonic vibration;
   an electrical stimulation device that generates a therapeutic electrical current via piezoelectric effect when ultrasonically vibrated by said means for generating ultrasonic vibration for treating said body tissue, said therapeutic electric current having a therapeutic voltage and amperage, the device to be disposed in the vicinity of the tissue to be treated;
an electrode disposed on said electrical stimulation device; and
a sensor in communication with said means for generating said ultrasonic vibration;
wherein said current is directly discharged from said electrode into said tissue to be treated and said device stops generating therapeutic electrical current when said ultrasonic vibration is stopped.

4. An apparatus for treating body tissue, comprising:
a ceramic motor that generates a therapeutic electrical current via piezoelectric effect when ultrasonically vibrated for treating said body tissue; and
electrodes disposed on said ceramic motor for discharging said therapeutic electrical current directly from said ceramic motor into said body tissue;
wherein said apparatus is adapted to be disposed in the vicinity of the tissue to be treated.

* * * * *